United States Patent [19]

Augurt

[11] Patent Number: 5,066,464
[45] Date of Patent: Nov. 19, 1991

[54] PREVACUUM STEAM STERILIZATION TEST PACK

[75] Inventor: Thomas A. Augurt, New Canaan, Conn.

[73] Assignee: Propper Manufacturing Company, Inc., Long Island City, N.Y.

[21] Appl. No.: 466,048

[22] Filed: Jan. 17, 1990

[51] Int. Cl.$^5$ ............................................. G01N 25/14
[52] U.S. Cl. ........................................ 422/58; 422/85; 422/87; 422/60; 436/1; 436/2
[58] Field of Search ..................... 422/58, 60, 85, 87; 436/1, 2

[56] References Cited

U.S. PATENT DOCUMENTS

| | | |
|---|---|---|
| 3,884,641 | 5/1975 | Kraffczyk et al. ............ 422/58 |
| 4,115,068 | 9/1978 | Joslyn . |
| 4,486,387 | 12/1984 | Augurt . |
| 4,576,795 | 3/1986 | Bruso . |
| 4,579,715 | 4/1986 | Bruso . |
| 4,594,223 | 6/1986 | Dyke et al. . |
| 4,596,696 | 6/1986 | Scoville, Jr. . |
| 4,692,307 | 9/1987 | Bruso . |

*Primary Examiner*—David L. Lacey
*Assistant Examiner*—Abanti B. Singla
*Attorney, Agent, or Firm*—Amster, Rothstein & Ebenstein

[57] ABSTRACT

A Bowie and Dick type prevacuum steam sterilization test pack for insertion into a sterilization chamber for indicating the presence of unacceptable levels of uncondensable gas comprises a housing, a heat sink and an indicator. The housing defines a single chamber having a large open end, a relatively small closed end opposite the open end, and a sidewall smoothly tapering from the open end to the closed end. The heat sink is disposed in the chamber and extends substantially from the open end to the closed end to define a path through which the steam travels from the open end toward the closed end, the path being adapted to provide sufficient exposure of the steam to the heat sink so that the steam condenses within the path, releasing any noncondensable gas associated with the steam, forcing the noncondensable gas so released toward and concentrating such noncondensable gas within the closed end. An indicator is disposed in the chamber adjacent the closed end for indicating the presence of noncondensable gas concentrated therein.

14 Claims, 2 Drawing Sheets

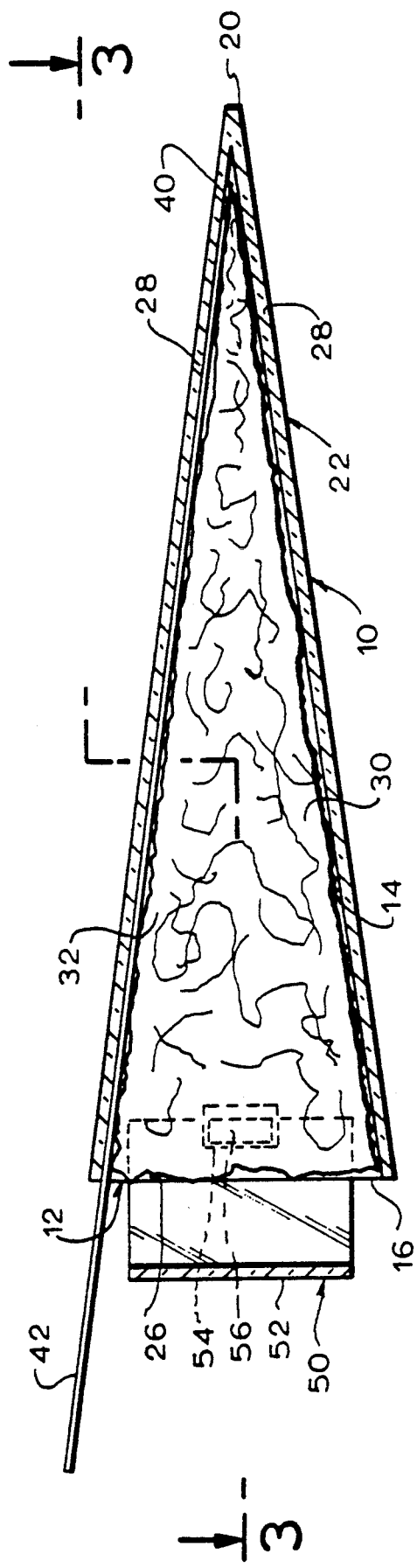
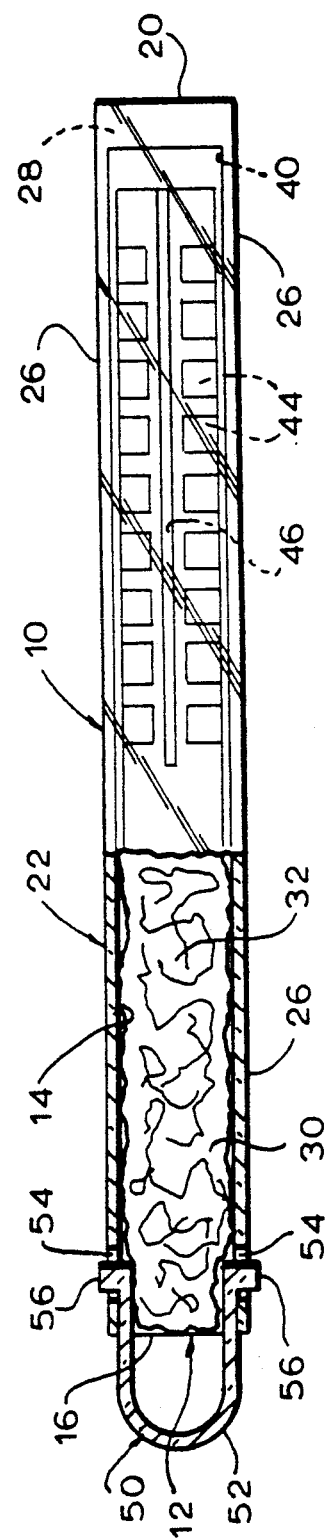

PREVACUUM STEAM STERILIZATION TEST PACK

BACKGROUND OF THE INVENTION

This invention relates generally to the sterilization of medical and surgical products, and more specifically to a disposable test pack adapted to be processed through a conventional sterilization cycle in a prevacuum steam sterilizer to check the proper operation of the sterilizer.

In the sterilization of medical dressings and instruments by steam, such dressings or instruments are conventionally assembled in bundles or packs and placed in a steam sterilization chamber which is sequenced through an appropriate sterilization cycle. Individual packages may contain stacks of towels, dressings, sponges and similar materials or may contain desired complements of surgical instruments or equipment for specific surgical procedures.

A current method of steam sterilization practice involves the placement of such packs in a sterilizer, the evacuation of air from the sterilizer and the introduction of saturated steam at a desired pressure to produce a desired temperature (typically 270°–276° F.) for a selected period of time. Prevacuum sterilizers operating in this manner have frequently replaced the downward displacement or gravity air discharge sterilizers previously used. The significant advantage of the prevacuum method is that removal of air before introduction of steam permits the rapid penetration of steam throughout the surgical pack. Elimination of air is necessary in all steam sterilizers since air trapped in the packages would prevent sterilization of the portion of the pack's interior where it collected. With the prevacuum method, the time required for steam penetration in a typical sterilization cycle is greatly reduced, and prevacuum sterilizers currently operate on a relative short cycle (with an exposure time on the order of 4 minutes at 134° C.). The operation of such sterilizers is well described in John J. Perkins, *Principles and Methods of Sterilization, in the Health Sciences*, published by Charles C. Thomas, Springfield, Ill., Chapter VI, "Prevacuum High Temperature Sterilization."

The ability to sterilize instruments in a shortened time, however, is dependent on the assumption that air is properly evacuated from the sterilizer. This includes the expectation that the vacuum system is functioning properly to evacuate the chamber initially and that there are no air leaks in the sterilizer or the vacuum lines which would permit introduction of air after the vacuum is drawn. During routine use, wear on certain sterilizer parts will eventually result in air leaks, and there is a need to test the sterilizer on a periodic (daily) basis to ascertain whether the vacuum system is functioning properly.

In 1961, a test procedure was proposed by J. Dick et al. and described by J. H. Bowie, et al. of the Department of Microbiology, Royal Infirmary, Edinburgh, Scotland in an article appearing in *The Lancet*, Mar. 16, 1963, pp. 586–587, which suggested a protocol for determining that the sterilizer was in proper working order, and that the vacuum system was operating properly. As indicated in the article, residual air in the system at the time steam is introduced will be swept by the steam pressure into the pack, usually to the pack center. Trapped air in the pack inhibits proper steam penetration.

According to the Bowie and Dick protocol, sterilization indicating tape was used in combination with a stack of surgical towels to test the working order of the sterilizer on a daily basis. Sterilization indicating tape is an adhesive tape having printed on its top surface stripes of a sterilization indicator material which has the property of changing color, for example from white to black, upon exposure to steam at an appropriate temperature for an appropriate period of time. According to the Bowie and Dick protocol, such tape was placed on a fabric sheet in a cross configuration, and the fabric sheet was then placed within a stack of folded surgical towels. The entire assembly was placed within the sterilizer. The sterilizer was run through its usual cycle with an exposure time of three and one-half minutes at 133°–134° C., after which the tape cross was examined to determine whether steam had completely penetrated the towel stacks effectively. A uniform color change was indication of a pass, and the presence of incompletely changed indicator color was a failure.

This protocol is currently in widespread use and is described in the *Association For The Advancement Of Medical Instrumentation (AAMI) Recommended Practice: Good Hospital Practice for Steam Sterilization and Sterility Assurance*, published by the AAMI, 1901 North Ft. Myer Drive, Suite 602, Arlington, Va. 22209. As indicated in Paragraph 7.8 of that publication, entitled "Prevacuum Sterilizer Residual Air Test," the test involves the use of 100% cotton huckaback towels, freshly laundered but not ironed (in view of the fact that excess dryness may affect the test results) folded in a 9"×12" configuration and piled 10"–11" high. The details of the Bowie and Dick procedure are described in the above-referenced *Recommended Practice*.

The testing of prevacuum sterilizers according to the Bowie and Dick protocol involves a number of important shortcomings. Firstly, the test is subject to individual execution by the sterilization section of the hospital on a daily basis, and the various requirements of the Bowie and Dick protocol—namely the type of towels or other fabrics used, their condition, age and the like (all of which affect the significance of the test result)—may vary widely from day to day and from institution to institution. Secondly, the performance of the Bowie and Dick protocol is relatively inconvenient and costly in that the expense of laundering towels (which cannot be thereafter used without relaundering), assembling the test arrangement and the like involve costly hospital labor. Additionally, certain hospitals have elected to eliminate laundry facilities entirely, utilizing only single-use disposable fabrics for their procedures, making the proper conduct of the Bowie and Dick protocol more inconvenient.

Attempts have been made to permit the use of a test sheet without the use of the conventional stacks of cotton towels in accordance with the Bowie and Dick protocol. As indicated on the literature on the Bowie and Dick protocol, various types of defects are most frequently found in sterilization equipment. Principal among these are (1) inadequacy of initial vacuum, leaving residual air within the packs and (2) air leaks within the chamber or vacuum system which permit the re-entrainment of air after a vacuum has been drawn. In designing a test pack to evaluate both these types of flaws, as well as others, it was discovered that there are a variety of different constraints operating.

For example, to the extent a flaw is present in the vacuum system which prevents a sufficient vacuum from being formed in the first instance, a test pack having a low porosity and/or high bulk is more likely to reveal a flaw of this type than one having a high porosity and/or lower bulk. As the vacuum is drawn, the air within the test pack tends to be drawn out of the pack. Low porosity and/or very bulky material surrounding the test sheet would tend to increase the difficulty of removal of such air and increase the likelihood that the test pack would indicate a flaw.

On the other hand, flaws caused by leaks involve the introduction of air into the sterilizer after the vacuum has been drawn. In this situation, the relationship between the porosity of the material surrounding the test sheet and sensitivity of the test is the reverse. The less porous and/or more bulky the material surrounding the test sheet, the less likely it is that air introduced into the sterilizer after the vacuum has been drawn (as in the case of a leak) will re-enter the test pack. Accordingly, with respect to a flaw resulting from air leaks after a sufficient vacuum has been drawn, low porosity material surrounding the test sheet would tend to make it more difficult for air from such a leak to enter the pack and decrease the likelihood that such a test pack would indicate a flaw.

In order to properly test the sterilizer, a test pack must provide an appropriate, but not excessive challenge to the vacuum system using as a guideline the challenge provided by the currently accepted towel pack standard for the Bowie and Dick protocol. It is desirable to design a relatively small, inexpensive and disposable test pack which achieves a challenge to the sterilizer comparable to the challenge provided by the accepted Bowie and Dick protocol.

Exemplary of the various attempts to provide a Bowie and Dick-type test pack are the test packs described in U.S. Pat. Nos. 4,486,387; 4,576,795; 4,579,715; 4,596,696; and 4,692,307. For example, according to U.S. Pat. No. 4,486,387, a disposable test pack is composed of a sterilization test sheet having defined areas adapted to change color in response to the presence of steam under selected exposure conditions, surrounded by a set of disposable nonwoven porous sheets of material arranged in overlying relation above and below the test sheet. The innermost sheets of material form an inner core region around the test sheet, and the remaining sheets form an outer shell region, with the porosity and bulk of the inner core region and the porosity of the outer shell region being selected so as to define a desirable challenge to the sterilizer.

The test pack of U.S. Pat. No. 4,486,387 is designed to be used according to the accepted Bowie and Dick protocol and to be placed in an otherwise empty sterilization chamber, sequenced through a predetermined cycle and removed. The pack is then opened and the interior test sheet examined for evidence of inadequate steam penetration, air bubbles and like defects. The presence of such defects indicates faults in the vacuum or other systems within the sterilization unit which require evaluation and repair. The test is intended to be performed on a daily basis with the interior test sheet forming a permanent record of such testing. The nonwoven sheet material and the remainder of the pack are disposed of after a single use.

Such a test pack provides detection of the common sterilizer flaws in a manner comparable to the Bowie and Dick protocol. Nonetheless, these test packs have not been found to be entirely satisfactory. Their complex construction requires a large number of sheets to be arranged in appropriate sequence and number and then packaged with overwrap or placed in an outside container providing a predetermined tightness. The complexity of the construction and the care required in assembling the same adds to the cost of the product. While the test packs are generally about the size of a 5" cube and thus substantially smaller than the towel packs required by the Bowie and Dick protocol, they are still relatively bulky when stored in quantity for daily tests. Furthermore, removal of the interior test sheet for storage as a permanent record requires unwrapping of the test pack or its removal from an outer container, followed by separation of the sheets to expose the interior test sheet. Indeed, the test results are not even known until this procedure is followed so that the interior test sheet can be inspected.

U.S. Pat. No. 4,594,223 discloses a test pack which simulates the Bowie and Dick protocol without the use of a plurality of porous and/or nonporous sheets arranged in particular sequences or heights and which enables the test sheet to be readily and immediately viewed and subsequently removed for storage as a permanent record without unwrapping of the test pack and separation of the sheets thereof. On the other hand, because of its concern with the possibility of condensed moisture from the steam affecting the final results, the patent teaches the use of a complex two-chamber test pack, with a large first chamber exposed to the sterilization chamber and containing a heat sink, and a communicating smaller second chamber containing the test sheet. While the test sheet can be read without destruction of the device, the two chambers must be broken apart to allow removal of the test sheet from the small chamber if it is to permanently stored. Thus the test pack is not capable of being reused. Additionally, the positioning of the generally rectangular smaller chamber relative to the generally cylindrical larger chamber provides corners, ledges and recesses where air bubbles may be trapped within the larger chamber so that they do not affect the results evidenced by the test sheet in the smaller chamber, thereby leading to possible false passes.

It is an object of the present invention to provide a relatively small, inexpensive and disposable test pack for use in prevacuum steam sterilizers to determine whether the sterilizer is functioning in accordance with proper standards by simulating air evacuation and steam penetration conditions of the conventional pack described in the Bowie and Dick protocol so as to define an appropriate challenge for a residual air test in a prevacuum sterilizer.

Another object is to provide such a test pack for prevacuum sterilizers which provides a repeatable and consistent standard for testing the working order of the sterilizer from day to day and from sterilizer to sterilizer, yet requires neither assembly by hospital personnel nor the use of hospital linen or laundries for its initial use.

A further object is to provide such a test pack which permits ready and immediate viewing of the test sheet and its removal for storage without destruction or disassembly of the test pack.

It is also an object of the present invention to provide such a test pack which is devoid of corners, recesses and ledges within or against which air bubbles may be trapped, leading to possible false passes.

It is another object to provide such a test pack which has a reusable housing permitting remanufacture of the test pack.

The above and related objects of the present invention are obtained in a device adapted for insertion into a sterilization chamber for indicating the presence of unacceptable levels of noncondensable gas. The device comprises a housing, a heat sink and an indicator means.

SUMMARY OF THE INVENTION

It has now been found that the above and related objects of the present invention are obtained in a device adapted for insertion into a sterilization chamber of a prevacuum steam sterilizer for indicating the presence of unacceptable levels of uncondensable gas. The device comprises a housing, a heat sink and an indicator means. More particularly, the housing defines a single chamber having a large open end, a relatively small closed end opposite the open end, and a sidewall smoothly tapering from the open end to the closed end. The heat sink is disposed in the chamber and extends substantially from the open end to the closed end, the heat sink being adapted to absorb latent heat from the steam until the temperature of the heat sink is in equilibrium with the ambient sterilizer temperature. The open end is adapted for open communication with the sterilization chamber when the device is inserted therein such that the steam enters the heat sink. The heat sink defines a path through which the steam travels from the open end toward the closed end, the path being adapted to provide sufficient exposure of the steam to the heat sink so that the steam condenses within the path, releasing any noncondensable gas associated with the steam, forcing the noncondensable gas so released toward and concentrating such noncondensable gas within the closed end. Means are disposed in the chamber adjacent the closed end for indicating the presence of noncondensable gas concentrated therein.

The device preferably additionally includes closure means secured to the housing adjacent the open end for operatively impeding passage of the heat sink through the open end without operatively impeding the passage of noncondensable gas, steam, and the indicating means through the open end. The housing and the closure means are cooperatively configured and dimensioned such that the device will, on a flat surface and under the influence of gravity, assume an orientation with the closed end no higher than the highest point of the open end. The closure means may be removably secured to the housing to enable replacement of the indicator means and heat sink and thus reuse of the housing.

In a preferred embodiment, the inner surface of the chamber is devoid of any obstruction to the communication of the steam and noncondensable gas between the open and closed ends. Thus the sidewall may taper linearly, and the chamber be generally triangular in cross section. The heat sink comprises a filler material of predetermined aggregate permeability and is made of a heat-conducting material defining a tortuous path. The indicating means is a heat and humidity sensitive chemical indicator, preferably a strip having one face abutting the sidewall and the opposite face abutting the heat sink. The strip is frictionally engaged in the chamber by the sidewall and the heat sink and extends outwardly from the open end, the strip being removable from the chamber without destruction of the housing or removal of the heat sink from the chamber. The housing is preferably made of a transparent material so that the indicating means is viewable through the transparent material.

BRIEF DESCRIPTION OF THE DRAWING

The above brief description, as well as further objects and features of the present invention, will be readily fully understood by reference to the following detailed description of the presently preferred, albeit illustrative, embodiments of the present invention when taken in conjunction with the accompanying drawing wherein:

FIG. 2 is a sectional view of the heat sink; and

FIG. 3 is a view thereof, partially in cross section, taken along the line 3—3 of FIG. 2.

DETAILED DESCRIPTION OF THE PREFERRED EMBODIMENTS

Figure 1:
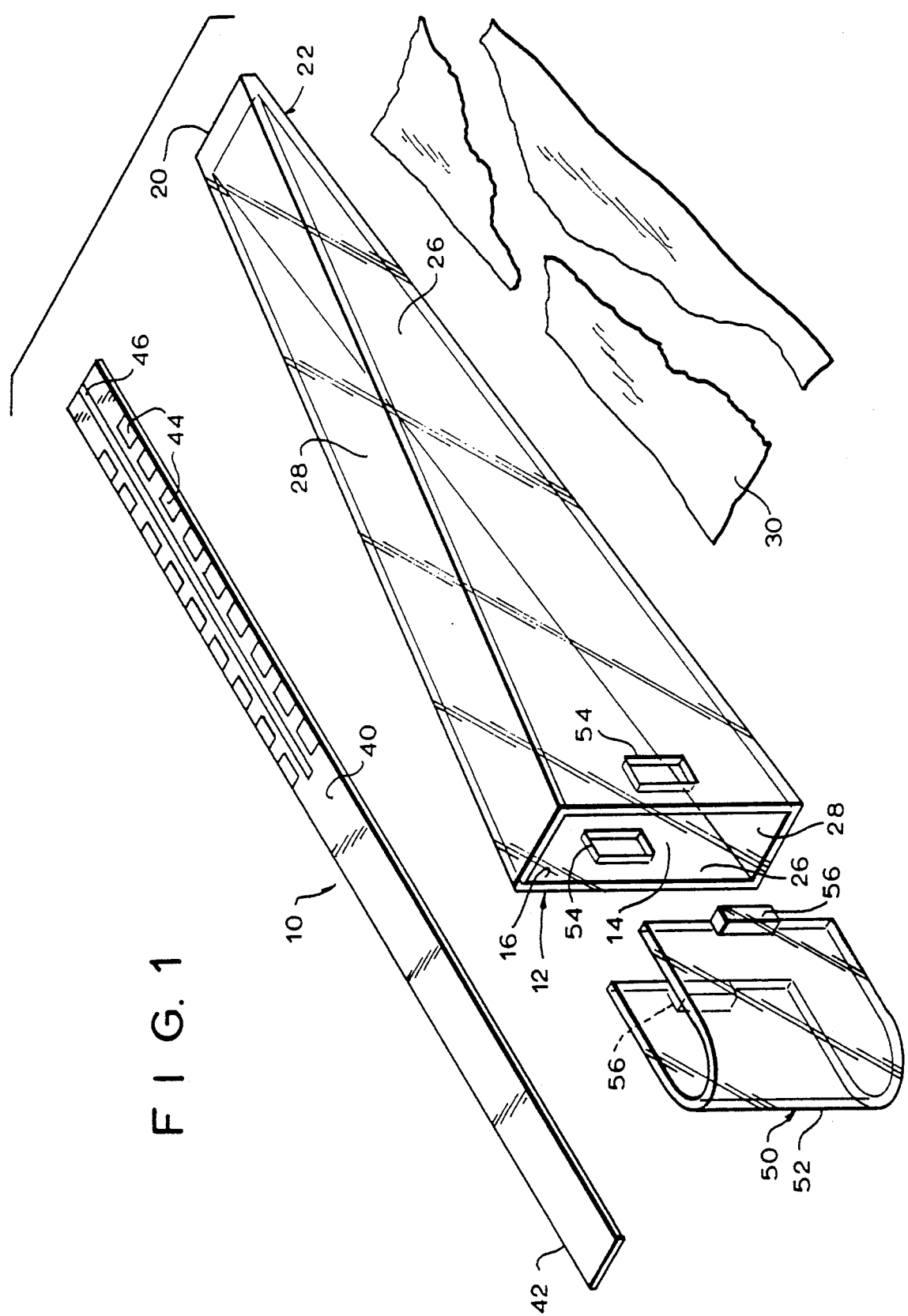
FIG. 1 is an exploded isometric view of a text pack according to the present invention, with the heat sink being shown fragmentarily.

Referring now to the drawing, and in particular to FIGS. 1-3 thereof, therein illustrated is a prevacuum steam sterilization test pack according to the present invention generally designated by the reference numeral 10. The test pack 10 is adapted for insertion into a steam sterilization chamber (not shown) and is especially suited to detect the presence of noncondensable gas, such as air, in the sterilization chamber during processing. It is contemplated that the device will be used to detect air leaks in the sterilizer or to detect any deficient evacuation in the prevacuum phase of a sterilization cycle.

The test pack 10 includes a housing generally designated 12 defining a single interior chamber 14 having a large throat or open end 16 which will be exposed during use to the ambient atmosphere of the sterilization chamber, a relatively small closed end 20 opposite the open end 16 which will receive collected noncondensable gas, and a sidewall generally designated 22 smoothly tapering from the open end 16 to the closed end 20 for concentrating the noncondensable gas within the chamber 14 at the closed end 20. The sidewall 22 preferably tapers linearly to provide an interior chamber 14 which is generally tirangular in cross section, formed by an opposed pair of flat triangular faces 26 and an opposed pair of flat rectangular sides 28 connecting the faces 26. The housing outer dimensions are preferably 7" in length (from end to end)×2" in width (at the open end 16)×0.75" height (from face to face). As the sidewall 22 is typically relatively thin, the housing inner dimensions (i.e., the chamber dimensions) approximate the housing outer dimensions. Both the configuration and the dimensions of the chamber may be varied broadly in order to present an appropriate challenge to the sterilizer. Thus the housings 12 may be polygonal or conical; the sidewalls 22 may taper linearly (that is, in a straight line), hyperbolically or exponentially and may even be composed of one or more arcuate segments, or the like.

The essential constraint on the configuration of the housing is that the inner surface of the chamber sidewall smoothly tapers from a large open end to a relatively small closed end and is devoid of any obstruction to the communication of the steam and noncondensable gas between the open and closed ends. Thus the chamber inner surface is devoid of any ledges, flanges, recesses or projections extending inwardly toward the interior of the chamber where they might constitute a shelter or trap for air bubbles, thereby giving rise to possible false pass readings by reducing the quantity of noncondensable gas concentrated in the closed end.

The housing 12 is economically formed by injection molding of a plastic or like material into the desired configurations and dimensions for the housing. The housing material is necessarily selected for stability in the presence of the elevated temperatures and humidities to be encountered in the sterilization chamber; thus the plastic should exhibit structural stability at a temperature of 280°–290° and a vacuum of about 12 millimeters of mercury. The housing material must also be chemically inert to the materials used on the indicator strip, as defined hereinafter. In addition, for reasons which will be evident hereinafter, the housing mateiral is preferably transparent. Preferred plastics include polypropylene, polycarbonate and the like. For reasons of material cost, ease of manufacture, and ruggedness, as well as the avoidance of possible air bubble traps, the housing is preferably of integral one-piece construction.

A heat sink 30 is disposed in the chamber 14 of the housing 12 and extends substantially from the open end 16 to the closed end 20. The heat sink 30 is adapted to absorb latent heat from the steam until the temperature of the heat sink is in equilibrium with the ambient sterilizer temperature. The heat sink 30 defines a path 32 through which steam from the sterilization chamber entering the open end 16 may travel along from the open end 16 toward the closed end 20. The path 32 is preferably a tortuous one adapted to provide sufficient exposure of the steam to the heat sink 30 so that the steam condenses within the path, thereby releasing any noncondensable gas (such as air) associated with the steam, forcing the noncondensable gas so released toward and concentrating the noncondensable gas within the closed end 20. The heat sink 30 is formed of a thermally insulative material in order to prevent the latent heat released by the steam from reaching the end of the indicator strip adjacent the closed end 20 too quickly and has a predetermined average or bulk permeability to resist to a desired level the passage therethrough of steam and noncondensable gas. A variety of materials may be used for the heat sink including polyurethane foam, crepe paper or fabrics such as muslin, percale or the like. The quantity of heat sink 30 within the chamber 14 is one of the factors which will vary the challenge. Preferably a flat sheet of 20"×20" heat sink material having a basis weight of 33.5 lbs. (per 3,000 sq. ft.²) and a bulk Frazier permeability of 5 cu. ft./min./sq. ft. air at 0.5 in. water may be crumpled and stuffed into a chamber having dimensions of 7"×2"×⅞" to provide a suitable challenge. The mass provides the heat sink effect necessary for condensation of the steam and condensables, and the porosity provides resistance to the passage of steam and non-condensables through the material. A good level of water repellancy (preferably about 12.0 using the water head method) is desirable so that the material does not compact too much on the introduction of steam. Like the housing material, the heat sink material must be chemically stable under the anticipated conditions of elevated temperature and humidity so as to not release chemicals which might have an adverse effect on the indicator strip. A preferred heat sink material is the non-woven Central Supply (C.S.) or sterilization wrap available under the tradename Steri-Wrap (available from Propper Manufacturing Co., Inc. of Long Island City, N.Y. 11101). A preferred foam for use as the heat sink material is a non-reticulated urethane polyester-type foam which because of its walled pore structure provides the necessary resistance to the passage of steam and air therethrough while still providing sufficient porosity for the purposes of the present invention. The preferred non-reticulated urethane foam has at least 20 ppi (pores per linear inch) and a density of about two pounds per board foot or greater.

Indicator means 40 are disposed in the chamber 14 adjacent the closed end 20 thereof for indicating the presence of noncondensable gas concentrated therein. The indicator means 40 is preferably a heat- and humidity-sensitive indicator strip which is adapted to change color, for example, from white to black, upon exposure to a predetermined temperature and humidity for a period of time. The indicator strip 40 may be any suitable known indicating means which may be employed to indicate the presence of a predetermined level of noncondensable gas (e.g., air) in a given environment. The indicator strip means 40 has one face thereof abutting a sidewall 22 of the housing and the opposite face thereof abutting the heat sink 30, so that the strip 40 is frictionally engaged in the chamber 14 by and between the sidewall 22 and the heat sink 30 to retain the indicator strip 40 in position against accidental displacement. Preferably an end 42 of the indicator strip 40 extends outwardly through the open end 16 so that the extending end 42 may be grasped and pulled on to remove the indicator strip 40 from the chamber 14 for retention as a permanent record, without the need for physical destruction of the housing 12 or removal of the heat sink 30 from the chamber 14. As earlier noted, the housing 12 is preferably made of a transparent material so as to enable the indicator strip 40 to be read immediately through the transparent material of the housing 12 (especially a side 28), even before it is removed from the chamber 14. The indicator strip 40 is typically flexible to enable it to conform to the inner surface of the housing sidewall 22 and thereby facilitate its being reading through the sidewall, but may alternatively be shaped to be flush against a shaped sidewall, also to facilitate reading thereof (for example, the strip 40 have a curved face matching the curve of a curved sidewall 22). Preferably the indicator strip 40 has a plurality of longitudinally spaced non-transferable color patches 44, which will change from an initial color to a final color under appropriate sterilizer conditions to signify a "pass," with a reference bar 46 of the desired final color being provided for comparative purposes. During assembly of the test pack 10, the indicator strip 40 is conveniently disposed in the chamber 14 prior to insertion of the heat sink 30.

The test pack 10 preferably additionally includes closure means generally designated 50 and secured to the housing 12 adjacent the open end 16 for operatively impeding passage of the heat sink 30 through the open end 16 without operatively impeding the passage of noncondensable gas, steam and the indicator strip 40 through the open end 16. As illustrated, the closure means 50 comprises a U-shaped piece 52 of the same material used to form the housing 12. The sidewall faces 26 adjacent the closed end 20 define apertures 54 and the closure means 50 defines an outwardly biased flange 56 on each leg thereof, the flanges 56 being configured and dimensioned to be received within the face apertures 54 to maintain the closure means 50 in position on the housing 12 against accidental displacement. To this end, the closure means 50 is constructed to provide the requisite degree of resilient flexibility to enable initial flexing of the closure 50 so as to permit the flanges 54 to pass through openend 16 and be positioned within the face apertures 56 and thereafter to bias outwardly the flanges 56 so as to maintain the engagement between the flanges 56 and apertures 54.

While it is possible for the closure means 50 to be permanently secured to the housing 12—for example, by using sonic welding or adhesive means—preferably the closure 50 is only releasably secured to the housing 12 so that the closure means 50 may be at least partially separated therefrom (e.g., at least pivoted away from the housing open end 16) to permit removal of the heat sink 30 from the housing chamber 14 and the substitution of a new indicator strip 40 and new heat sink 30 within the chamber 14 prior to re-assembly of the closure 50 and housing 12. While it is the intention of the present invention that the small, easy to use and inexpensive test pack 10 of the present invention be disposed of after each use, it is recognized that on occasion it may be necessary to reuse the housing 12 in connection with appropriate fresh indicator strips 40 and appropriate fresh (or in certain instances laundered) heat sink material 30 in rare instances, and even that some institutions may prefer to do so as a regular practice, maintaining a supply of indicator strips 40 and heat sinks 30 for this purpose. Such re-assembly of the test pack may be termed "remanufacture."

Preferably, the closure means 50 serves an additional function totally unrelated to its closure function. Thus, the housing 12 and closure means 50 are cooperatively configured and dimensioned such that the test pack 10 will, on a flat surface and under the influence of gravity, assume an orientation with the closed end 20 no higher than the highest point of the open end 16. As the closure means 50 is preferably U-shaped in cross section so that it cannot serve as a stable base for the test pack 10 with the closed end 20 pointing upwardly. When placed in this upright position alone in a sterilizer chamber, the test pack 10 will re-orient itself under the influence of gravity by falling over onto one its faces 26 so that the open end 16 and closed end 20 thereof are level. Even if the test pack 10 is deliberately place on one of its sides 28, the closed end 20 will be generally at the same height as the lowest point of the open end 16 and no higher than the highest point of the open end 16. The advantage of this non-upright configuration of a test pack during use is that air within the chamber 14, which is intended to be concentrated at the closed end 20 does not have to fight gravity to reach the closed end 20, as would be the case if the test pack 10 were in an upright position (with the closed end 20 at the highest point) since air is heavier than steam.

As the pressure in the sterilization chamber forces steam through open end 16 and through the tortuous path 32 of heat sink 30, the steam repeatedly gives up its latent heat and collapses, or condenses, into water. The collapse of steam creates a partial void along the path 32 containing any noncondensable gases. The void is immediately filled as steam continues to enter the path, and the advancing front of steam concentrates any residual air associated with the steam and forces it toward closed end 20. The advancing front of steam continues to give up its latent heat to the heat sink 30 until the temperature of the heat sink 30 is in equilibrium with the ambient sterilizer temperature.

The advancing front of steam forces residual air into closed end 20. The greater air concentration, and thus the greater shielding effect of the air around indicator strip 40, permits a progressively greater indication (i.e., unchanged color patches) on indicator strip 40. If there is a negligible quantity of air associated with the steam, little or no air will accumulate in closed end 20 when the steam condenses and the heat and humidity will contact the indicator strip 40, causing it to change color during the sterilization stage of the process. On the other hand, if there is appreciable quantity of air associated with the steam, the air will concentrate in closed end 20 and surround the adjacent end of the indicator strip 40, insulating or shielding the color patches 44 thereon from exposure to the humidity and latent heat of the steam.

The indicator strip 40 can be calibrated to change color only upon exposure to a quantity of heat and humidity over a period of time which could not be present in the closed end 20 if an unacceptable air leak rate existed. The volume of the closed end 20 can be varied to vary the resulting height of the air accumulated in closed end 20 to correspond to a scale for indicating unacceptable levels of air in the sterilization chamber, as can the placement of the changeable color patches 44 of indicator strip 40. The density ratio between the mass of the heat sink material 30 and the volume of the chamber 14 can be controlled to provide a standard resistance to penetration of the material by the steam. The resistance should be such that the steam will condense in the path 32. Among the many other variables affecting the severity of the challenge are the effective size of the throat or open end 16, the length of the housing from end to end, etc.

At the end of the sterilization stage, test pack 10 is removed from the sterilization chamber, and indicator strip 40 is read. Optionally, the indicator strip 40 is removed from chamber 14 without disassembly or destruction of housing 12 and closure means 50. The strip 40 can be retained as a permanent record for quality control purposes to compare the sterilization cycles over time.

EXAMPLE

A paper indicator strip 9×⅜ in. in size was placed against one of the ⅞×6¾ in. rectangularly shaped sides of a wedge-shaped, rigid polycarbonate plastic container having a length of 6¾ in. and a square shaped throat opening 1 13/16×⅞ in. in size. Along one approximately 3 in. long section the indicator strip contained several parallel lines of steam-reactive chemical imprint, each 7/16 in. wide, spaced 3/16 in. apart. The white steam-reactive indicator lines were printed parallel with the narrow edge of the paper strip. At the center of the same section of the paper strip, a black reference line was printed running parallel with the long side of the strip. The black color of the reference line was selected so that, when the steam-reactive chemical imprints underwent a color change reaction in the presence of pure pressurized, saturated steam, they would change to a color at least as dark as the black reference line.

The container was then stuffed to the tip (i.e., the closed end) with a 20×20 in. piece of Steri-Wrap brand non-woven paper-like sheet, known in the industry as a C.S. or sterilization wrap. The sheet was compacted by hand pressure to fill the container except for approximately the last ¼ in. of the open throat end. Care was exercised so that the indicator strip was not wrinkled or shifted, and that it remained stretched along the rectangular side of the container. Approximately 2 inches of the strip remained projecting out of the open throat end.

A U-shaped closure was applied to partially close the open throat end.

Test packs so prepared were subject to Bowie and Dick tests in test cycles designed to produce conditions inside a pre-vacuum steam sterilizer similar to what would be present in a sterilizer accepted to be functioning correctly as well as conditions which would simulate incorrect functioning by allowing relatively large amounts of air residuals to be present in the chamber. By alternating evacuation and steam purging steps, the amount of air residuals in a 225 liter sterilizer chamber were reduced to less than 100 ml. of air for the simulation of a correct cycle and to 600 or more ml. of air for the simulation of a faulty cycle.

In a correct cycle all the steam-reactive indicator lines changed to a black color at least as dark as the pre-printed black reference line. In an incorrect cycle a number of the steam-reactive indicator lines remain unchanged or changed only to a brown color.

To verify the accuracy of the test results, comparative tests were carried out using the conventional towel test pack described by Bowie and Dick in their original publication and test packs of alternate construction already demonstrated to be equivalent to the same. In all instances the results with the test packs of the present invention were the same as with the towel pack and the other test packs. Complete color changes occurred in correct cycles, and incomplete color changes occurred in faulty cycles.

Thus, the test pack of the present invention serves the very purpose of the Bowie and Dick test in detecting sterilizers in which the steam varies from the desired 100% saturated steam required for correct steam sterilization and either is superheated (instead of saturated) or contains air or other inert gases (because of boiler problems or leaky sterilizers). There is, however, another condition which is considered undesirable, although it is not expected to endanger the sterilization process. This condition is "wet steam" wherein the steam contains liquid water droplets which cause everything placed in the sterilizer to come out wet, sometimes dripping wet. In severe cases, wet steam can adversely effect the strength of the indicator strip and cause the indicator strip to stick strongly to the side of the housing, the combined effect of these two factors being that it becomes difficult or impossible to pull the indicator strip out of the housing without tearing it. Additionally, the wet steam can cause adhering of the printing and chemical imprints to the housing. It will be appreciated that none of these problems associated with wet steam interfere with the obtaining of proper readings on the indicator strip, but only present a problem when it is desired to remove the indicator strip from the housing for record-keeping purposes or for reuse of the housing. If it is desired to overcome these problems associated with the presence of wet steam, a special indicator strip may be used which is saturated with a polymer latex to increase its wet strength and overcoated with a non-stick coating to reduce sticking of the indicator strip to the side of the housing and in particular sticking of the ink or the chemical imprints thereon to the housing side. A preferred latex-treated paper for use in such a special indicator strip is the Type 8631 paper available from the Premoid Division of James River Corporation. An indicator strip formulated from such a latex-treated paper and coated with a silicone or fluorosilicone coating (such as those available from Dow-Corning) remains intact and easily removable from the housing even through the wettest sterilization cycles using wet steam.

To summarize, the present invention provides a relatively small, inexpensive and disposable test pack for use in prevacuum sterilizers, to simulate air evacuation and steam penetration conditions of the conventional pack described in the Bowie and Dick protocol and define an appropriate challenge. The test pack provides a repeatable and consistent standard, and permits and ready and immediate viewing of the test sheet as well as its removal for storage without destruction and disassembly of the test pack, so that the housing thereof may be reused (e.g., to remanufacture the test pack). The test pack is devoid of obstructions which may trap air bubbles, leading to possibly false passes.

Now that the preferred embodiments have been shown and described in detail, various modifications and improvements thereon will become readily apparent to those skilled in the art. Accordingly, the appended claims are to be construed broadly and in a manner consistent with the spirit and scope of the invention described herein.

I claim:

1. A device adapted for insertion into a sterilization chamber of a prevacuum steam sterilizer for indicating the presence of unacceptable levels of noncondensable gas comprising:
   (A) a housing defining a single hollow elongate chamber having an open end, a closed end wherein said open end is larger than said closed end, and wherein said open end and said closed end are disposed opposite one another, said housing further comprising continuously, a sidewall tapering from said open end to said closed end;
   (B) a heat sink disposed in said chamber and extending substantially from said open end to said closed end, said heat sink constructed so as to absorb latent heat from steam until the temperature of said heat sink is in equilibrium with ambient sterilizer temperature;
   said open end constructed so as to be in flow communication with the sterilization chamber when said device is inserted therein such that when steam enters said heat sink through said open end, said heat sink defines a plurality of tortuous paths through which the steam travels from said open end to said closed end, so as to provide sufficient exposure of the steam to said heat sink so that the steam condenses within said heat sink, releasing any noncondensable gas associated with the steam, forcing the noncondensable gas so released toward and concentrating such noncondensable gas within said closed end; and
   (C) means disposed in said chamber adjacent said closed end for indicating the presence of noncondensable gas concentrated therein.

2. The device of claim 1 wherein the inner surface of said chamber is devoid of any obstruction to the communication of the steam and noncondensable gas between said open and closed ends.

3. The device of claim 1 wherein said sidewall tapers linearly, and said chamber is generally triangular in cross section.

4. The device of claim 1 additionally including closure means secured to said housing adjacent said open end for operatively impeding passage of said heat sink through said open end without operatively impeding the passage of noncondensable gas, steam, and said indicating means through said open end.

5. The device of claim 4 wherein said housing and said closure means are cooperatively configured and dimensioned such that the device will, on a flat surface and under the influence of gravity, assume an orientation with said closed end no lower than the lowest point of said open end.

6. The device of claim 4 wherein said closure means is removably secured to said housing to enable replacement of said indicator means and heat sink and thus reuse of said housing.

7. The device of claim 1 wherein said heat sink comprises a filler material of predetermined aggregate permeability.

8. The device of claim 1 wherein said indicating means is a heat and humidity sensitive chemical indicator.

9. A device adapted for insertion into a sterilization chamber of a prevacuum steam sterilizer for indicating the presence of unacceptable levels of noncondensable gas comprising:
(A) a housing defining a single hollow elongate chamber having a open end, a closed end wherein said open end is larger than said closed end and wherein said open end and said closed end are disposed opposite one another, said housing further comprising a sidewall continuously tapering from said open end to said closed end;
(B) a heat sink disposed in said chamber and extending substantially from said open end to said closed end, said heat sink constructed so as to absorb latent heat from steam until the temperature of said heat sink is in equilibrium with ambient sterilizer temperature;
said open end constructed so as to be in flow communication with the sterilization chamber when said device in inserted therein such that the steam enters said heat sink, said heat sink defining a plurality of tortuous paths through which the steam travels from said open end toward said closed end, so as to condense the steam within said heat sink, releasing any noncondensable gas associated with the steam, forcing the noncondensable gas so released toward and concentrating such noncondensable gas within said closed end; and
(C) means disposed in said chamber adjacent said closed end for indicating the presence of noncondensable gas concentrated therein,
said indicating means being a generally planar strip having one face abutting said sidewall and the opposite face abutting said heat sink.

10. The device of claim 9 wherein said strip is frictionally engaged in said chamber by said sidewall and said heat sink and extends outwardly from said open end, said strip being removable from said chamber without destruction of said housing or removal of said heat sink from said chamber.

11. The device of claim 9 wherein said housing is made of a transparent material, and said indicating means is viewable through said transparent material.

12. A device adapted for insertion into a sterilization chamber of a prevacuum steam sterilizer for indicating the presence of unacceptable levels of noncondensable gas comprising:
(A) a transparent housing defining a single hollow elongate chamber having an open end, a closed end wherein said open end is larger than said closed end and wherein said open end and said closed end are disposed opposite one another said transparent housing further comprising a sidewall continuously tapering from said open end to said closed end, the inner surface of said chamber being devoid of any obstruction to the communication of steam and noncondensable gas between said open and closed ends;
(B) a heat sink disposed in said chamber and extending substantially from said open end to said closed end, said heat sink constructed so as to absorb latent heat from steam until the temperature of said heat sink is in equilibrium with the ambient sterilizer temperature, said heat sink comprises a filler material of predetermined aggregate permeability and heat-conduction and constructed so as to define a plurality of tortuous paths;
said open end constructed so as to be in flow communication with the sterilization chamber when said device is inserted therein such that the steam enters said heat sink, and travels from said open end toward said closed end, so as to provide sufficient exposure of the steam to said heat sink so that the steam condenses within said heat sink, releasing any noncondensable gas associated with the steam, forcing the noncondensable gas so released toward and concentrating such noncondensable gas within said closed end;
(C) means disposed in said chamber adjacent said closed end for indicating the presence of noncondensable gas concentrated therein, said indicating means being a heat and humidity sensitive chemical indicator in the form of a generally planar strip having one face abutting said sidewall and the opposite face abutting said heat sink, said strip being frictionally engaged in said chamber by said sidewall and said heat sink and extending outwardly from said open end, said strip being removable from said chamber without destruction of said housing or removal of said heat sink from said chamber; and
(D) closure means secured to said housing adjacent said open end for operatively impeding passage of said heat sink through said open end without operatively impeding the passage of noncondensable gas, steam, and said indicating means through said open end, said housing and said closure means being cooperatively configured and dimensioned such that the device will, on a flat surface and under the influence of gravity, assume an orientation with said closed end no lower than the lowest point of said open end.

13. The device of claim 12 wherein said sidewall tapers linearly, and said chamber is generally triangular in cross section.

14. The device of claim 1 wherein said indicating means includes a plurality of longitudinally spaced color patches and a comparative reference color bar extending longitudinally along said plurality of color patches, said color patches changing from an initial color to a final color under appropriate sterilizer conditions to signify a pass, and said color bar being of the final color.

* * * * *